United States Patent
Hur et al.

(10) Patent No.: US 10,783,343 B2
(45) Date of Patent: Sep. 22, 2020

(54) FINGERPRINT RECOGNITION MODULE, ELECTRONIC DEVICE EMPLOYING SAME, AND METHOD FOR MANUFACTURING SOUND WAVE CONTROL MEMBER THEREFOR

(71) Applicant: KOREA INSTITUTE OF MACHINERY & MATERIALS, Daejeon (KR)

(72) Inventors: Shin Hur, Daejeon (KR); Kyung-jun Song, Daejeon (KR); Jun-hyuk Kwak, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 0 days.

(21) Appl. No.: 16/086,951

(22) PCT Filed: Mar. 31, 2017

(86) PCT No.: PCT/KR2017/003535
§ 371 (c)(1),
(2) Date: Sep. 20, 2018

(87) PCT Pub. No.: WO2017/176008
PCT Pub. Date: Oct. 12, 2017

(65) Prior Publication Data
US 2019/0102592 A1    Apr. 4, 2019

(30) Foreign Application Priority Data
Apr. 6, 2016   (KR) .................. 10-2016-0042493

(51) Int. Cl.
*G06K 9/00*       (2006.01)
*H03H 7/38*       (2006.01)
*A61B 5/1172*     (2016.01)

(52) U.S. Cl.
CPC .......... *G06K 9/0002* (2013.01); *A61B 5/1172* (2013.01); *H03H 7/38* (2013.01)

(58) Field of Classification Search
CPC .... G06K 9/0002; G06K 9/00; G06K 9/00013; A61B 5/1172; H03H 7/38; G07C 9/00071; G07C 9/00563
(Continued)

(56) References Cited

U.S. PATENT DOCUMENTS 5,438,554 A * 8/1995 Seyed-Bolorforosh ...................... B06B 1/0622
                                                                                  310/320
5,553,035 A * 9/1996 Seyed-Bolorforosh ...................... B06B 1/0622
                                                                                  310/320

(Continued)

FOREIGN PATENT DOCUMENTS

KR    1020090085579 A    8/2009
KR    1020150080812 A    7/2015

(Continued)

OTHER PUBLICATIONS

International Search Report for PCT/KR2017/003535 dated May 23, 2017, citing the above reference(s).

*Primary Examiner* — Edwin C Holloway, III
(74) *Attorney, Agent, or Firm* — Hauptman Ham, LLP

(57) ABSTRACT

In a module for detecting a fingerprint, an electronic device using the module and a method for manufacturing an acoustic control member for the module, the module includes a contact member, a transducer, an impedance matching member, an acoustic control member and a signal processor. A fingerprint makes contact with the contact member. The transducer outputs an ultrasonic signal to the contact member and receives the ultrasonic signal reflected from the contact member. The impedance matching member (Continued)

is charged between the contact member and the transducer, to transmit the ultrasonic signal between the contact member and the transducer. The acoustic control member is inserted between the contact member and the transducer. The impedance matching member is charged inside of the acoustic control member. The signal processor makes electric contact with the transducer, to sense the fingerprint based on the received ultrasonic signal.

12 Claims, 11 Drawing Sheets

(58) Field of Classification Search
USPC ........ 340/5.52, 5.82; 382/124; 310/334, 335
See application file for complete search history.

(56) References Cited

U.S. PATENT DOCUMENTS

| | | | | |
|---|---|---|---|---|
| 5,563,345 A | * | 10/1996 | Kersten | A61B 5/1172 |
| | | | | 382/124 |
| 6,645,150 B2 | * | 11/2003 | Angelsen | B06B 1/0614 |
| | | | | 600/459 |
| 2010/0066207 A1 | * | 3/2010 | Saito | A61B 8/4281 |
| | | | | 310/335 |
| 2012/0206585 A1 | * | 8/2012 | Schneider | G01N 29/06 |
| | | | | 348/77 |
| 2013/0135218 A1 | * | 5/2013 | Jain | G06F 3/0488 |
| | | | | 345/173 |
| 2013/0136321 A1 | * | 5/2013 | Lee | G06K 9/0002 |
| | | | | 382/124 |
| 2014/0312350 A1 | | 10/2014 | Schneider et al. | |
| 2015/0189136 A1 | * | 7/2015 | Chung, II | G06K 9/00013 |
| | | | | 348/77 |
| 2016/0288169 A1 | * | 10/2016 | Bae | B06B 1/0685 |

FOREIGN PATENT DOCUMENTS

| | | |
|---|---|---|
| WO | 2015012420 A1 | 1/2015 |
| WO | 2015068868 A1 | 5/2015 |

* cited by examiner

FINGERPRINT RECOGNITION MODULE, ELECTRONIC DEVICE EMPLOYING SAME, AND METHOD FOR MANUFACTURING SOUND WAVE CONTROL MEMBER THEREFOR

This application claims priority to Korean Patent Application No. 2016-0042492, filed on Apr. 6, 2016, and all the benefits accruing therefrom under 35 U.S.C. § 119, the content of which in its entirety is herein incorporated by reference.

BACKGROUND

1. Field of Disclosure

The present disclosure of invention relates to a module for detecting a fingerprint, an electronic device using the module and a method for manufacturing an acoustic control member for the module, and more specifically the present disclosure of invention relates to a module for detecting a fingerprint, an electronic device using the module and a method for manufacturing an acoustic control member for the module, capable of increasing recognition rate for an ultrasonic wave and increasing accuracy of detecting a fingerprint.

2. Description of Related Technology

Generally, a fingerprint recognition sensor is a sensor for detecting a fingerprint, and is widely used, such as a door locking device, a device for turning on or off an electric device, or a device for locking or unlocking a sleep mode.

The fingerprint recognition sensor may be divided into an ultrasonic type, an infrared type, a capacitance type, and so on, based on an operation type. Here, in the ultrasonic type, an ultrasonic signal from a plurality of piezoelectric sensors is reflected differently, due to a difference of acoustic impedance between a valley of a fingerprint and a ridge of the fingerprint, and then the reflected signal is measured by the piezoelectric sensors again to recognize the fingerprint.

Recently, a swipe type fingerprint recognition sensor manufactured with a relatively small volume is developed, so that the fingerprint recognition sensor may be used more widely on a mobile device.

Accordingly, as the minimization and the security problem for the fingerprint recognition sensor are to be important, the recognition rate is to be increased. Here, to the recognition rate is increased, sensibility of the piezoelectric sensor is to be increased, but the power consumption may be increased, the cost price for the piezoelectric sensor may be increased and a life span of the piezoelectric sensor may be decreased.

The related prior art is Korean laid-open patent application No. 2015-0080812, which is published on Jul. 10, 2015.

SUMMARY

The present invention is developed to solve the above-mentioned problems of the related arts. The present invention provides a module for detecting a fingerprint capable of increasing recognition rate for an ultrasonic wave and increasing accuracy of detecting a fingerprint.

In addition, the present invention also provides an electronic device using the module.

In addition, the present invention also provides a method for manufacturing an acoustic control member for the module.

According to an example embodiment of a module for detecting a fingerprint, the module includes a contact member, a transducer, an impedance matching member, an acoustic control member and a signal processor. A fingerprint makes contact with the contact member. The transducer outputs an ultrasonic signal to the contact member and receives the ultrasonic signal reflected from the contact member. The impedance matching member is charged between the contact member and the transducer, to transmit the ultrasonic signal between the contact member and the transducer. The acoustic control member is inserted between the contact member and the transducer. The impedance matching member is charged inside of the acoustic control member. The signal processor makes electric contact with the transducer, to sense the fingerprint based on the received ultrasonic signal.

In an example, the impedance matching member may include a first matching member charged to the acoustic control member, and a second matching member charged between the contact member and the acoustic control member, or between the acoustic control member and the transducer.

In an example, the acoustic control member may include a first signal transmitting groove formed on a surface facing one of the contact member and the transducer, a second signal transmitting groove formed on a surface facing the remaining of the contact member and the transducer, and a connecting line connecting the first signal transmitting groove with the second signal transmitting groove. The impedance matching member may be charged to the first signal transmitting groove, the second signal transmitting groove and the connecting line.

According to an example embodiment of an electronic device, the electronic device includes the module for detecting the fingerprint, a main controller and a converting controller. The main controller controls the electronic device, based on the signal detected by the signal processor. The converting controller converts the signal detected by the signal processor, and transmits the converted signal to the main controller.

According to an example embodiment of a method for manufacturing the acoustic control member, the method includes a first etching step, a second etching step, a third etching step, a first bonding step, a second bonding step and a matching charging step. In the first etching step, a first member is etched to form the first signal transmitting groove. In the second etching step, a second member is etched to form the connecting line. In the third etching step, a third member is etched to form the second signal transmitting groove. In the first bonding step, the first member is bonded with the second member via a bonding member. In the second bonding step, the second member is bonded with the third member via the bonding member. In the matching charging step, the impedance matching member is charged to the first signal transmitting groove, the second signal transmitting groove and the connecting line.

In an example, in the first etching step, the first member may be etched to further form the connecting line partially.

In an example, in the third etching step, the third member may be etched to further form the connecting line partially.

In an example, in the second etching step, the second member may be etched to further form a buffer space having a diameter different from the connecting line.

In an example, the method may further include a fourth etching step and a third bonding step. In the fourth etching step, a fourth member may be etched to further form a buffer space having a diameter different from the connecting line. In the third bonding step, the second member and the fourth member may be alternately bonded with each other via the bonding member based on a position of the buffer space. In the first bonding step, the first member may be bonded on a first surface of a base member after the third bonding step, via the bonding member. In the second bonding step, the third member may be bonded on second surface of the base member after the third bonding step, via the bonding member.

According to another example embodiment of a method for manufacturing the acoustic control member, the method a height determining step, a hole forming step, a partially charging step and a finishing step. In the height determining step, at least two stacked members are sequentially formed on a first surface of a base member. In the hole forming step, the base member and the stacked members are respectively etched based on a stacked order of the stacked member. In the partially charging step, the impedance matching member is charged to every portion etched in the hole forming step. In the finishing step, the base member is manufactured to expose the impedance matching member through a second surface of the base member. The height determining step, the hole forming step and the partially charging step are repeated according to a height of the acoustic control member.

In an example, the finishing step may include a manufacturing step in which the second surface of the base member is entirely etched to expose the impedance matching member.

In an example, the finishing step may further include a groove forming step in which a groove is formed on the second surface of the base member to expose the impedance matching member, and a final charging step in which the impedance matching member is charged to the groove formed in the groove forming step.

According to the present example embodiments, sensibility of the signal processor is increased to increase a recognition rate of the ultrasonic wave and to increase a reliability for recognizing the fingerprint.

In addition, transmissivity of the ultrasonic wave, reflectivity of a reverberation wave and transmittance of a destruction wave are increased according to a combination of the contact member, the impedance matching member and the acoustic control member.

In addition, even though a wavelength and an amplitude of the destruction wave is decreased because of the reflection of the ultrasonic wave due to the fingerprint, the destruction wave may be stably transmitted to the signal processor.

In addition, the ultrasonic wave incident from the acoustic control member is stably transmitted, the ultrasonic wave is induced to be resonated in the acoustic control member, and the incident ultrasonic wave is amplified, so that the ultrasonic wave may be stably transmitted between the contact member and the signal processor.

In addition, the impedance matching member is charged to the etched portion of the acoustic control member, so that the ultrasonic wave may be prevented from being attenuated and may be amplified.

In addition, the security in recognition of the fingerprint by the electronic device may be increased and the person information stored in the electronic device may be stably protected.

In addition, a micro machining may be performed to control the acoustic in the ultrasonic range, so that the acoustic control member may be easily manufactured.

In addition, each structure having each function in the stacked structure of the acoustic control member may be classified in detail, and the stacking and the bonding between the members of the acoustic control member may be easily performed.

In addition, a centering between the first signal transmitting groove, the second signal transmitting groove and the connecting line formed in the acoustic control member may be easily performed, and stacking error may be minimized to increase the reliability of the acoustic control member.

In addition, the height of the acoustic control member may be decreased, and thus the module for detecting the fingerprint may be minimized and manufactured with relatively thinner thickness.

In addition, the impedance matching member is charged to the acoustic control member, and thus the impedance matching may be more increased in transmitting the ultrasonic wave, the structure of the acoustic control member may be more strengthened, and the structure may be more stably formed.

In addition, sweat pores, and valley and ridge of the finger may be correctly detected to simulate a stereoscopic image of the fingerprint.

In addition, the fingerprint may be recognized even though contaminants such as a dust, a sweat, a remained cosmetics and so on remain on the fingerprint. The fingerprint may be easily recognized regardless of the material of the contact member on which the fingerprint contacts, and thus the module may be manufactured with various kinds of designs.

In addition, the stereoscopic image may be obtained including a dermis layer and an epidermis layer of the fingerprint of human beings, and the real fingerprint and the counterfeit fingerprint may be easily recognized to increase the security.

In addition, the electronic device may have more increased security via extracting the characteristics of the fingerprint to be registered and certificated. Thus, high resolution fingerprint technology may be performed based on a low power ultrasonic wave.

In addition, the transducer uses PMUT so that the power of the ultrasonic wave may be more increased and the structure thereof may be more simplified, compared to CMUT.

In addition, the destruction wave disappearing in the reverberation wave in the fingerprint is amplified and is transmitted to the transducer, and the signal processor stably senses the destruction wave to increase the resolution of the image. Thus, the fingerprint image may be obtained more correctly with the same source as the conventional ultrasonic wave, the signal processor having relatively lower capacity may be used, and power consumption may be decreased.

Here, the main controller 200 may control the electronic device based on the signal detected by the signal processor 50. The main controller 200 may be electrically connected to the signal processor 50 via a flip chip bonding or an electrode formed through a via-hole.

The converting controller 300 converts the signal detected by the signal processor 50, and transmits the signal to the main controller 200.

Here, the signal detected by the signal processor 50 is converted into a signal used for controlling the electronic device, and then the converted signal is transmitted to the main controller 200.

The converting controller 300 may be electrically connected to the signal processor 50 and the main controller 200, via a flip chip bonding or an electrode formed through a via-hole.

Hereinafter, the module 100 will be explained.

Figure 1:
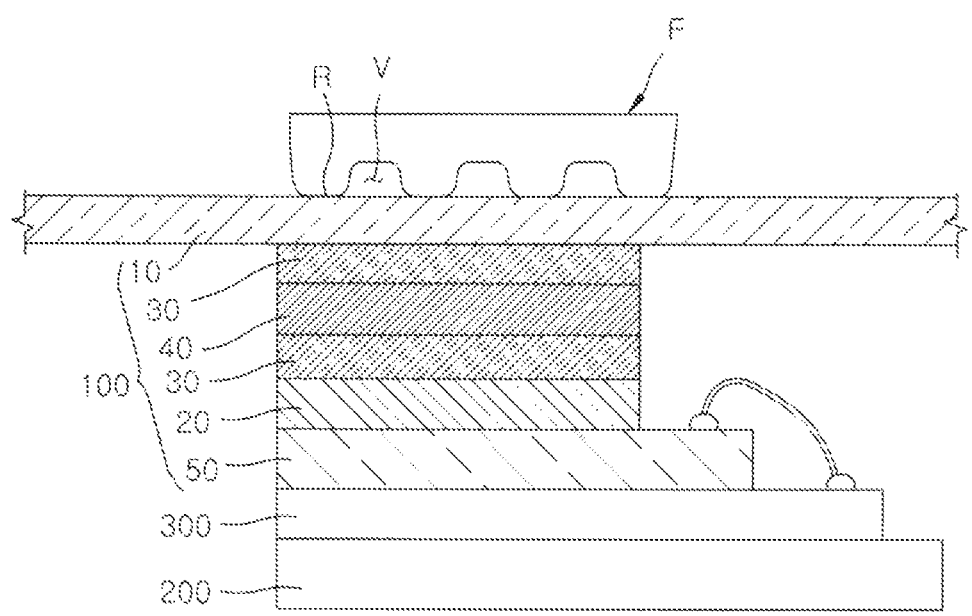
FIG. 1 is a cross-sectional view illustrating an electronic device according to an example embodiment of the present invention.
Figure 2:
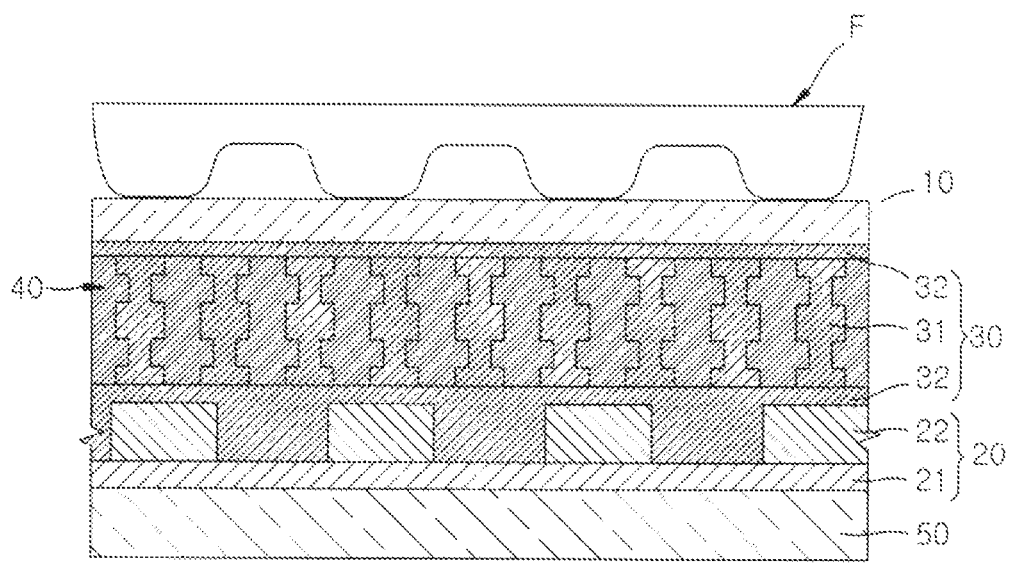
FIG. 2 is a cross-sectional view illustrating a module for detecting a fingerprint of the electronic device in FIG. 1.
Figure 3:
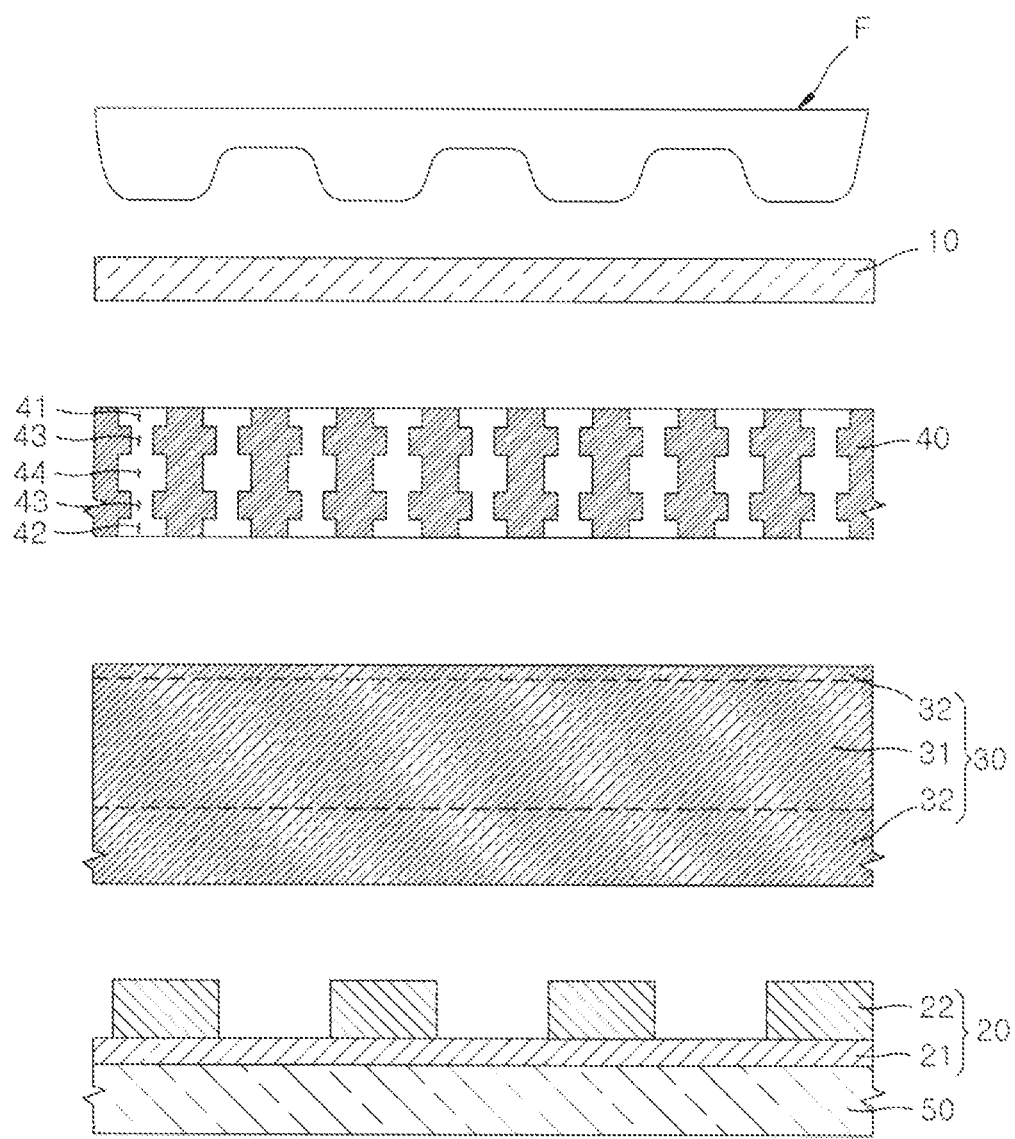
FIG. 3 is an exploded cross-sectional view illustrating the module for detecting the fingerprint of FIG. 2.
Figure 4A:
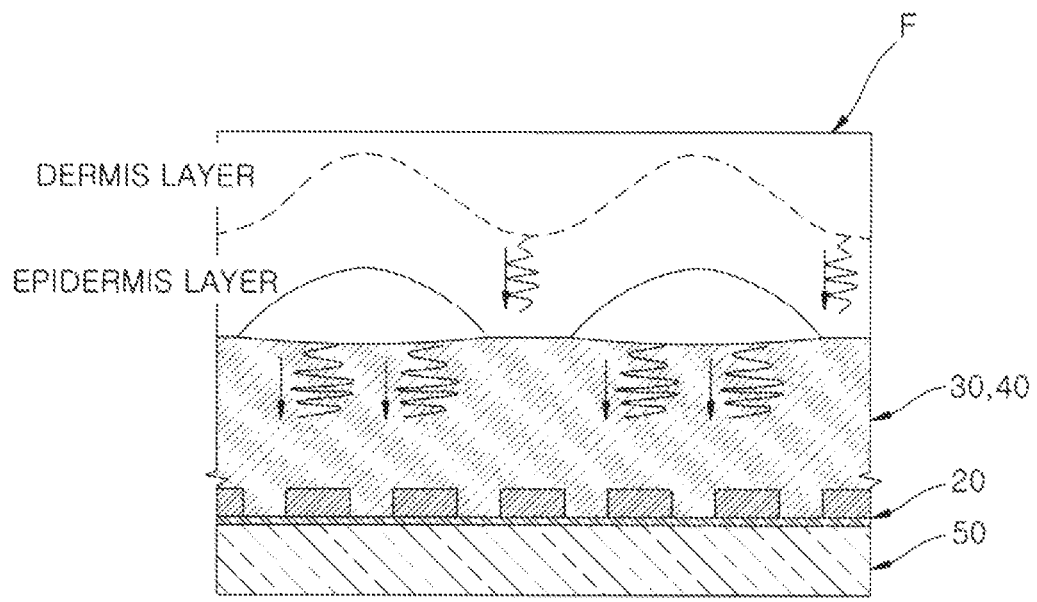
FIG. 4A and FIG. 4B are schematic views illustrating transmission of ultrasonic wave in the module of FIG. 2, when the fingerprint of human begins is recognized by the module of FIG. 2.
Figure 4B:
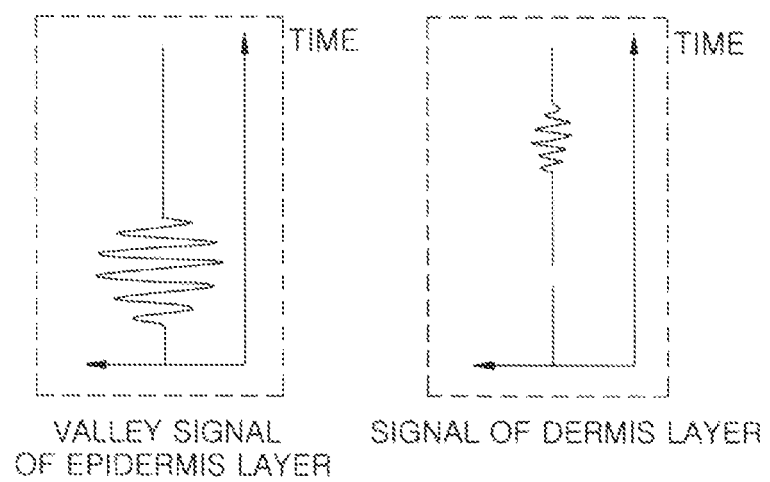

FIG. 2 is a cross-sectional view illustrating a module for detecting a fingerprint of the electronic device in FIG. 1. FIG. 3 is an exploded cross-sectional view illustrating the module for detecting the fingerprint of FIG. 2. FIG. 4A and FIG. 4B are schematic views illustrating transmission of ultrasonic wave in the module of FIG. 2, when the finger-

| * Reference numerals | | |
|---|---|---|
| 100: module | 200: main controller | 300: converting controller |
| 10: contact member | 20: transducer | 21: base layer |
| 22: piezo-sensor | 30: impedance matching member | 31: first matching member |
| 32: second matching member | 33: adhesive member | 40: acoustic control member |
| 41: first signal transmitting groove | 42: second signal transmitting groove | 43: connecting line |
| 44: buffer space | 50: signal processor | 60: base member |
| 61: first member | 62: second member | 63: third member |
| 64: fourth member | 65: stacked member | 66: bonding member |
| S11: first etching step | S12: second etching step | S13: third etching step |
| S14: fourth etching step | S21: first bonding step | S22: second bonding step |
| S23: third bonding step | S31: matching charging step | S1: height determining step |
| S2: hole forming step | S3: partially charging step | S4: finishing step |
| S41: manufacturing step | S42: groove forming step | S43: final charging step |
| F: fingerprint | F': counterfeit fingerprint | V: valley     R: ridge |

DETAILED DESCRIPTION

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Same elements or components are expressed with same reference numerals in the drawings.

FIG. 1 is a cross-sectional view illustrating an electronic device according to an example embodiment of the present invention.

Referring to FIG. 1, the electronic device according to the present example embodiment may strengthen the security thereof via a fingerprint F recognized by a module 100 for detecting a fingerprint (hereinafter, a module).

The electronic device includes the module 100 and a main controller 200, and may further include a convening controller 300.

The module 100 recognizes the fingerprint F using an ultrasonic wave, and will be explained below in detail.

Figure 5A:
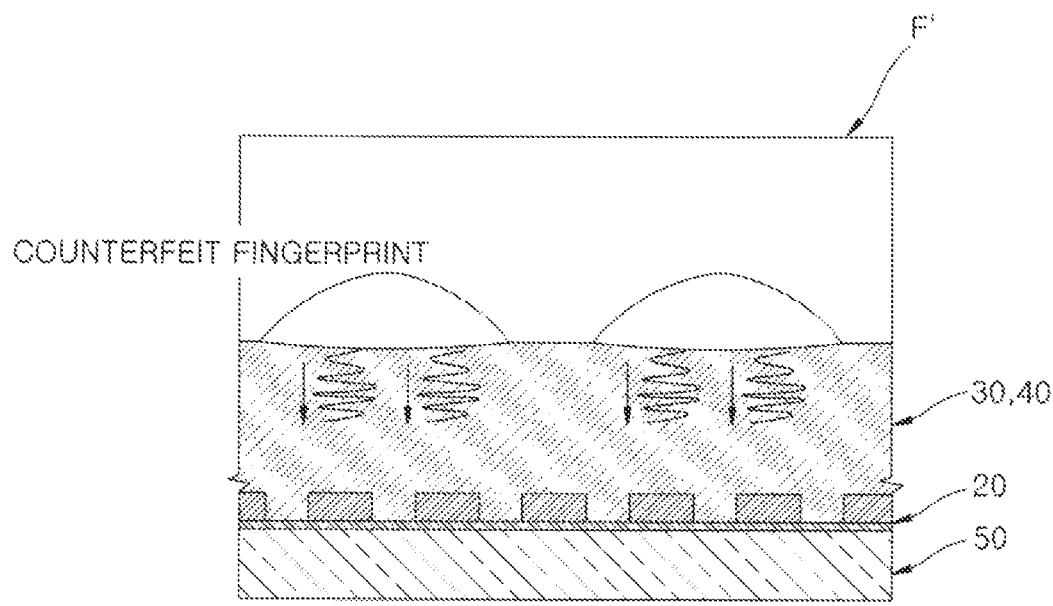
FIG. 5A and FIG. 5B are schematic views illustrating transmission of ultrasonic wave in the module of FIG. 2, when a counterfeit fingerprint is recognized by the module of FIG. 2.
Figure 5B:
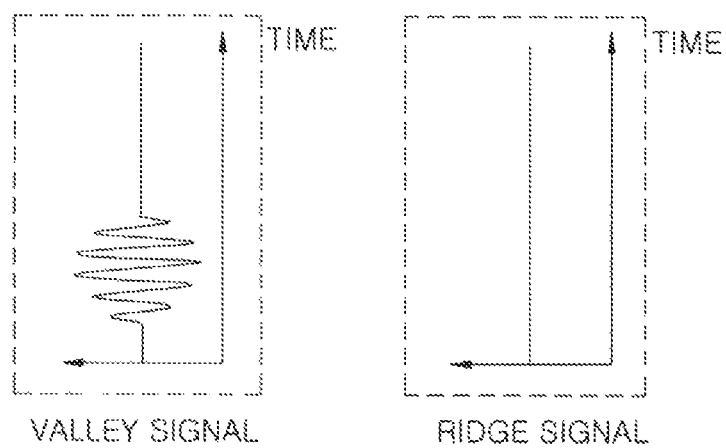
Figure 6:
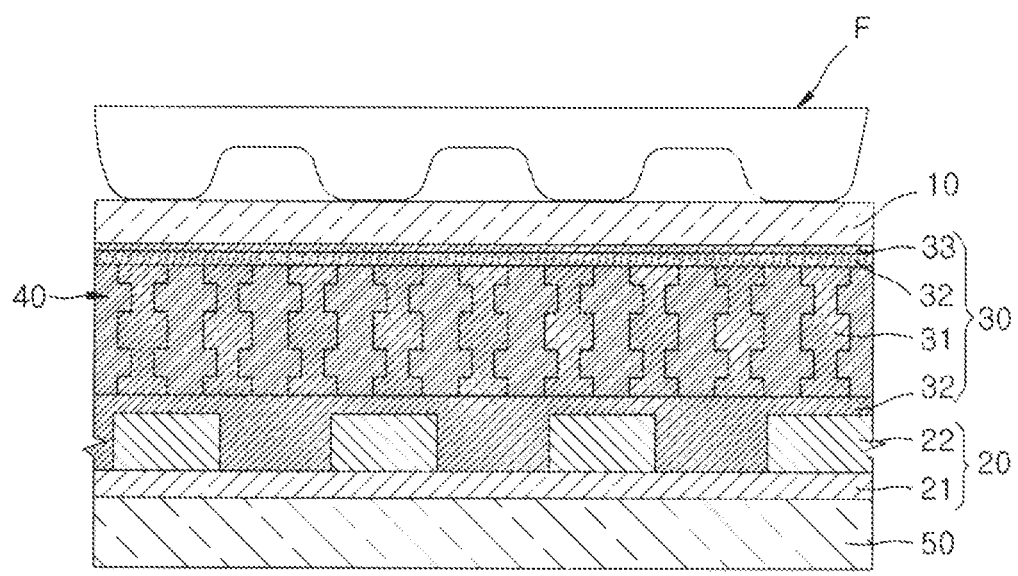
FIG. 6 is a cross-sectional view illustrating another module for detecting a fingerprint.

The main controller 200 controls the electronic device according to the signal detected by a signal processor 50 included in the module 100.

print of human begins is recognized by the module of FIG. 2. FIG. 5A and FIG. 5B are schematic views illustrating transmission of ultrasonic wave in the module of FIG. 2, when a counterfeit fingerprint is recognized by the module of FIG. 2. FIG. 6 is a cross-sectional view illustrating another module for detecting a fingerprint.

Referring to FIG. 2, FIG. 3, FIG. 4, FIG. 5 and FIG. 6, the module 100 according to the present example embodiment includes a contact member 10, a transducer 20, an impedance matching member 30, an acoustic control member 40, and a signal processor 50.

The fingerprint makes contact with the contact member 10. The contact member 10 may include a glass, aluminum, sapphire, a plastic and so on. The contact member 10 reflects an ultrasonic wave incident into the contact member 10.

The contact member 10 may be integrally formed with a touch screen device equipped to the electronic device or a display device. The contact member 10 may be used as a cover attached to a front surface of the touch screen device or the display device.

The transducer 20 outputs an ultrasonic wave signal to the contact member 10, and receives the ultrasonic wave signal reflected from the contact member 10. The transducer 20 may be a plural.

The transducer 20 may be a piezoelectric micro-machined ultrasonic transducer (PMUT) or a capacitive micro-machined ultrasonic transducer (CMUT).

The transducer 20 includes a piezo-sensor 22 and a base layer 21. The piezo-sensor 22 outputs the ultrasonic wave signal to the contact member 10, and receives the ultrasonic wave signal reflected from the contact member 10. A plurality of piezo-sensors 22 is arranged on the base layer 21. The base layer 21 may be replaced by the signal processor 50. In addition, an electrode may be formed on both surfaces of the piezo-sensors 22.

The impedance matching member 30 may be charged between the contact member 10 and the transducer 20. The impedance matching member 30 transmits the ultrasonic wave signal between the contact member 10 and the transducer 20. The impedance matching member 30 makes the transmission of the ultrasonic wave signal much easier, and matches the impedance between the transducer 20 and the fingerprint F.

The impedance matching member 30 includes a first matching member 31 and a second matching member 32. The first matching member 31 is charged to the acoustic control member 40. The second matching member 32 is charged between the contact member 10 and the acoustic control member 40, or between the acoustic control member 40 and the transducer 20.

For example, the second matching member 32 may be charged between the piezo-sensors 22 of the transducer 20, to prevent an air layer from being formed between the transducer 20 and the acoustic control member 40 and to transmit the ultrasonic wave more easily.

Alternatively, the second matching member 32 may bond the acoustic control member 40 with the transducer 20, or bond the acoustic control member 40 with the contact member 10.

In addition, the impedance matching member 30 may further include an adhesive member 33 charged between the contact member 10 and the acoustic control member 40 to bond the contact member 10 with the acoustic control member 40.

Thus, the impedance matching member 30 connects and fixes the transducer 20, the acoustic control member 40 and the contact member 10 with each other, to be integrally formed.

The impedance matching member 40 is inserted between the contact member 10 and the transducer 20. The impedance matching member 30 is charged inside of the acoustic control member 40. The acoustic control member 40 may amplify the ultrasonic wave signal transmitting to and receiving from the transducer 20.

The acoustic control member 40 may include Helmholtz resonator array structure, surface resonant effect in doubly negative or signal negative-mass meta-materials, Fabry-Perot (FP) resonant, Near-zero mass, anisotropic meta-material resonant tunneling type, and so on.

The acoustic control member 40 includes a first signal transmitting groove 41, a second signal transmitting groove 42, and a connecting line 43. The first signal transmitting groove 41 is formed on a surface facing one of the contact member 40 and the transducer 20. The second signal transmitting groove 42 is formed on a surface facing the remaining of the contact member 40 and the transducer 20. The connecting line 43 connects the first signal transmitting groove 41 with the second signal transmitting groove 42. Thus, the ultrasonic wave passes through the acoustic control member 40. The impedance matching member 30 is charged to the first signal transmitting groove 41, the second signal transmitting groove 42 and the connecting line 43, and thus the transmittance of the ultrasonic wave may be increased.

For example, diameters of the first signal transmitting groove 41, the second signal transmitting groove 42 and the connecting line 43 are substantially same with each other. Alternatively, diameters of the first signal transmitting groove 41 and the connecting line 43 are different from each other, and those of the second signal transmitting groove 42 and the connecting line 43 are different from each other.

In the present example embodiment, the diameters of the first signal transmitting groove 41 and the second signal transmitting groove 42 are substantially same with each other, and the diameter of the first signal transmitting groove 41 is larger than that of the connecting line 43.

In addition, a buffer space 44 may be formed in the acoustic control member 40, and is formed in a line with the connecting line 43. The diameter of the buffer space 44 is different from that of the connecting line 43. For example, the diameter of the buffer space 44 is larger than that of the connecting line 43. The impedance matching member 30 is charged to the buffer space 44.

The acoustic control member 40 may be manufactured via one of MEMS, NEMS, 3D printing and nano-imprinting.

The signal processor 50 makes electric contact with the transducer 20, and detects the fingerprint base on the ultrasonic wave signal received from the transducer 20. The signal processor 50 controls the transducer 20 to generate the ultrasonic wave, as the fingerprint F makes contact with the contact member 10. In addition, the transducer 20 may be integrally formed or mounted with the signal processor 50.

Here, the electric contact between the signal processor 50 and the transducer 20 is not limited thereto, and the base layer 21 is formed as the signal processor 50 so that the signal processor 50 and the transducer 20 are integrally formed with each other. Alternatively, the base layer 21 and the signal processor 50 make contact with each other, via a flip chip bonding, or the base layer 21 and the signal processor 50 are integrally formed with each other, via forming an electrode through a via-hole.

Hereinafter, an operation of the module is explained.

In the module 100, the signal processor 50, the transducer 20, the acoustic control member 40 and the contact member 10 are sequentially formed. Here, the first matching member 31 is charged to the acoustic control member 40.

In addition, the contact member 10 and the acoustic control member 40 are bonded with each other, via the second matching member 32 or the adhesive member 33. Here, the contact member 10 and the acoustic control member 40 are spaced apart from each other.

In addition, the acoustic control member 40 and the transducer 20 are bonded with each other, via the second matching member 32. Here, the contact member 10 and the acoustic control member 40 may be spaced apart from each other, or may be contacted with each other.

In the fingerprint F of human beings, the fingerprint F includes a valley V and a ridge R, and a length from a start of the valley V to an end of the ridge R is about 500 μm (between about 400 μm and about 600 μm). A width of the valley V is between about 100 μm and about 300 μm, and a height of the ridge R is between about 74 μm and about 150 μm.

In measuring the pattern of the fingerprint F using the ultrasonic wave, a magnitude of a transmitting wave depending on impedance characteristics (for example, a density, a transmitting velocity of a sound wave), and a magnitude of the reverberation wave are used.

Here, the impedance of a cell and the fingerprint F is about 1.5 Mrayl, and the impedance of an air is about 0.000428

Mrayl, and the impedance of the piezo-sensor 22 of the transducer 20 is about 30 Mrayl.

Thus, the impedance matching member 30 is charged between the transducer 20 and the contact member 10, for the impedance matching between the transducer 20 and the fingerprint F.

When the fingerprint F makes contact with the contact member 10, the ultrasonic wave is generated from the transducer 20, to be transmitted to the contact member 10.

The ultrasonic wave generated from the transducer 20 and the reverberation wave reflected from the contact member 10, pass through the acoustic control member 40, and thus have a frequency capable of almost 100% (between 90% and 100%, or between 95% and 100%) transmittance, due to resonance.

Then, as illustrated in FIG. 4, when the fingerprint F makes contact with the contact member 10, the transmitting wave is negligible and the reverberation is relatively large since the valley V has an air layer and the difference of the impedance is relatively large. However, the reverberation is relatively small since the ultrasonic wave is transmitted to the human beings.

In addition, the difference of the impedance between a dermis layer and an epidermis layer of the fingerprint of human beings is between about 10% and about 30%, and thus the wave reflected on the epidermis layer, and the wave passing through the epidermis layer and reflected on the dermis layer are generated. Thus, the pattern of the fingerprint may be imaged using time delay between the above waves inputted to the transducer 20.

Here, a minimum distance between two points required to differentiate two points at a diffraction limit of the sound wave, is a half of the wavelength. Thus, the diffraction limit determines the limit of space resolution of the imaging device, and the limit of the space resolution is due to the destruction wave disappearing among the reverberation having characteristics of an object.

However, in the present example embodiment, the destruction wave is amplified via passing the acoustic control member 40, and thus the pattern of the fingerprint on both of the epidermis layer and the dermis layer may be imaged with a stereoscopic image.

Then, in the imaged fingerprint, the valley V and the ridge R of the fingerprint may be expressed more correctly and the dermis layer and the epidermis layer may be distinct.

Accordingly, in the module of the present example embodiment, the destruction wave is amplified such that the fingerprint imaged with the stereoscopic image in the signal processor may be specified more correctly, and the resolution of the imaged fingerprint may be enhanced more.

In addition, as illustrated in FIG. 5, when a counterfeit fingerprint F' makes contact with the contact member 10, the reflection on the valley V and the ridge R of the counterfeit fingerprint F may be similar to the fingerprint F, but the difference between the dermis layer and the epidermis layer does not exist in the counterfeit fingerprint F' so that the stereoscopic image for the fingerprint may not exist or may be obscure.

Thus, in the module of the present example embodiment, the stereoscopic image for the fingerprint obtained from the module may be used to determine whether the fingerprint is counterfeited or not.

Hereinafter, a method for manufacturing the acoustic control member is explained.

Figure 7:
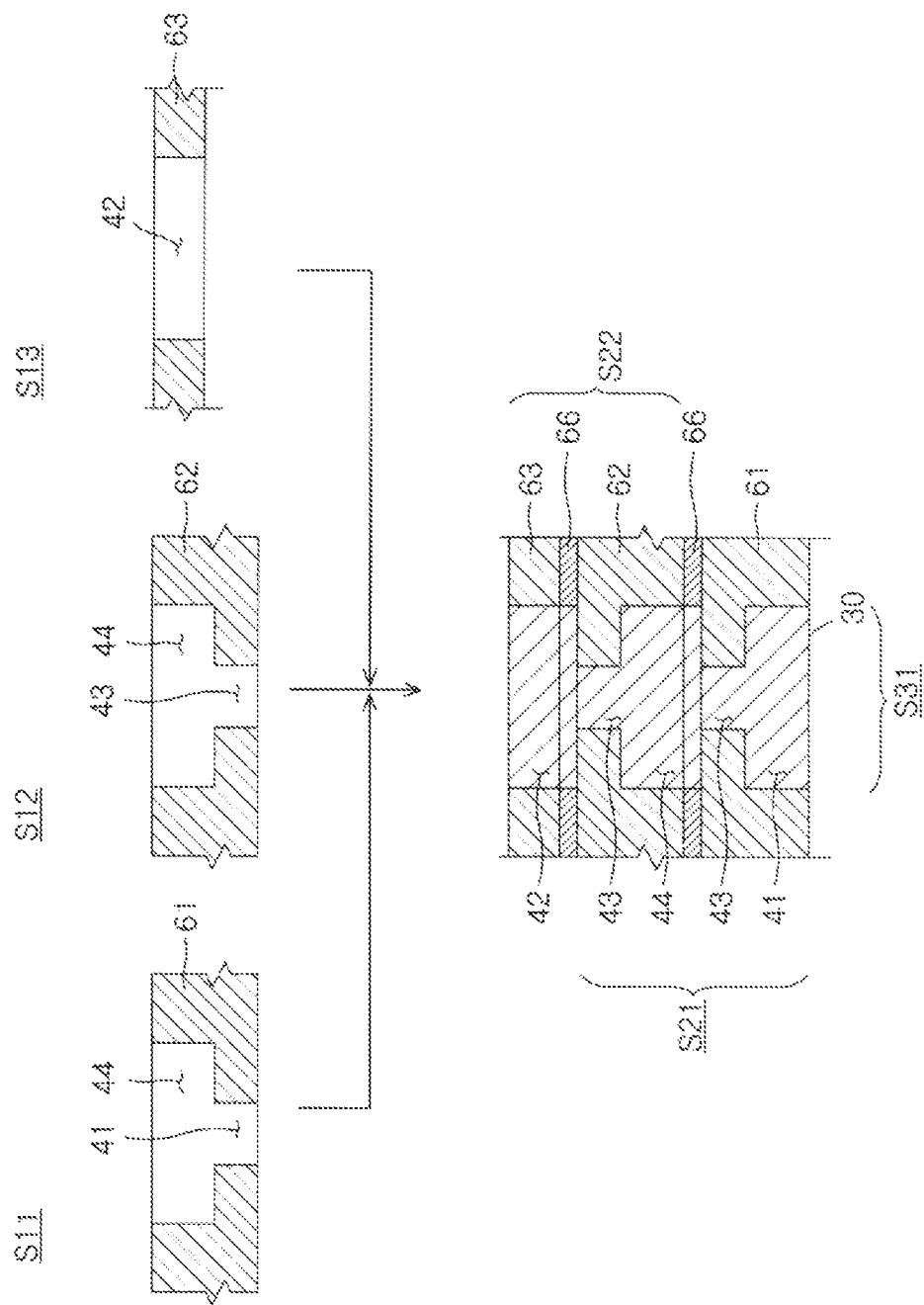
FIG. 7 is a series of cross-sectional views illustrating a method for manufacturing an acoustic control member according to another example embodiment of the present invention.
Figure 8:
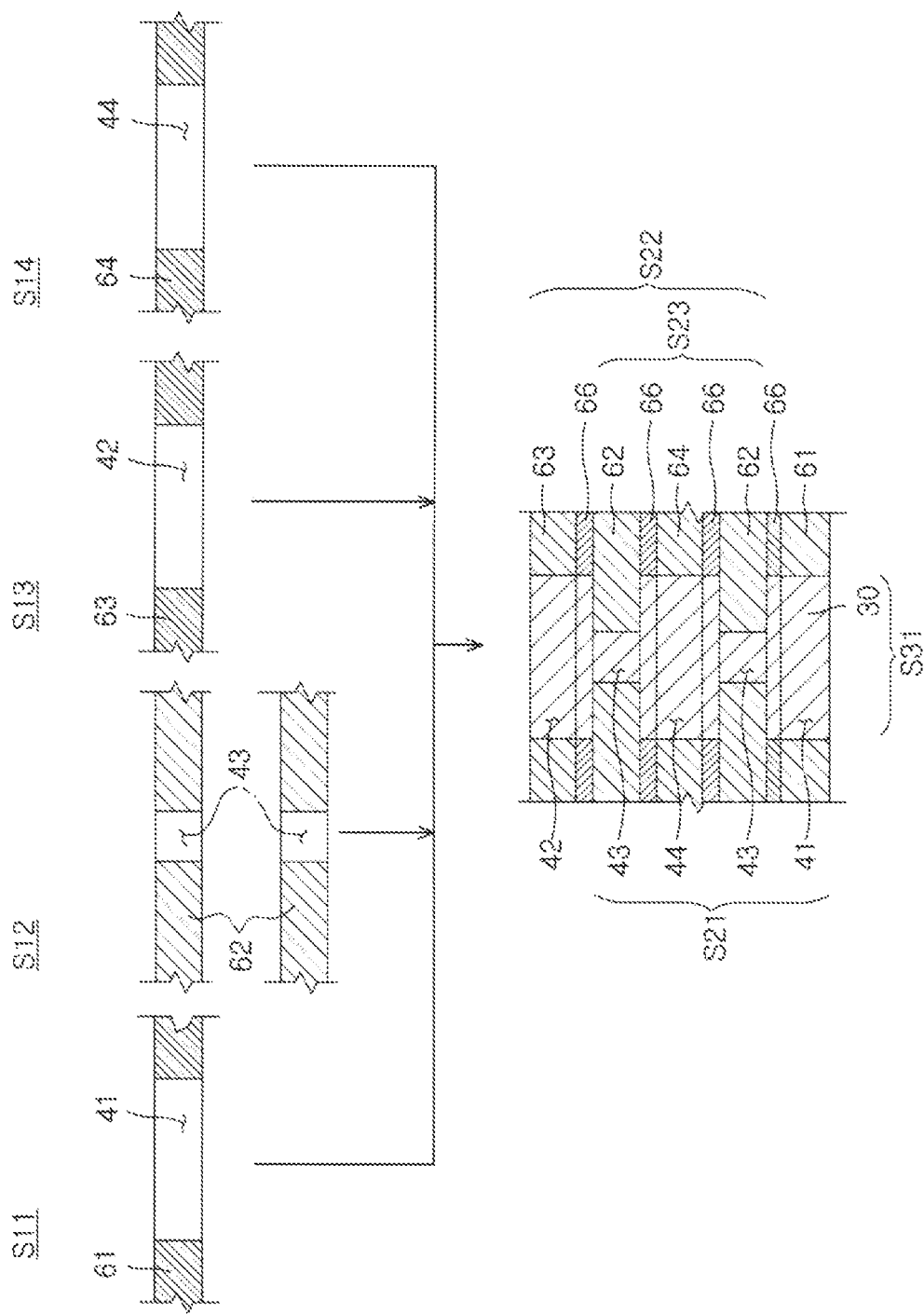
FIG. 8 is another series of cross-sectional views illustrating the method of FIG. 7.

FIG. 7 is a series of cross-sectional views illustrating a method for manufacturing an acoustic control member according to another example embodiment of the present invention. FIG. 8 is another series of cross-sectional views illustrating the method of FIG. 7.

The method for manufacturing the acoustic control member includes a first etching step S11, a second etching step S12, a third etching step S13, a first bonding step S21, a second bonding step S22 and a matching charging step S31.

In the first etching step S11, the first member 61 is etched to form the first signal transmitting groove 41. At least one first member 61 may be etched considering a depth of the first signal transmitting groove 41. Here, a plurality of first members 61 may be sequentially and vertically bonded via a bonding member 66. In the first etching step S11, the first member 61 may be etched to further form the connecting line 43 partially.

In the second etching step S12, the second member 62 is etched to form the connecting line 43. At least one second member 62 may be etched considering a length of the connecting line 43. Here, a plurality of second members 62 may be sequentially and vertically bonded via the bonding member 66.

In the third etching step S13, the third member 63 is etched to form the second signal transmitting groove 42. At least one third member 63 may be etched considering a depth of the second signal transmitting groove 42. Here, a plurality of third members 63 may be sequentially and vertically bonded via the bonding member 66. In the third etching step S13, the third member 63 may be etched to further form the connecting line 43 partially.

The steps mentioned above may be performed via a dry etching using a laser, or via a wet etching using an etchant.

In the first bonding step S21, the first member 61 is bonded with the second member 62 via the bonding member 66.

In the second bonding step S22, the second member 62 is bonded with the third member 63 via the bonding member 66.

Here, the buffer space 44 may be further formed in the connecting line 43, and the diameter of the buffer space 44 is different from that of the connecting line 43.

For example, as illustrated in FIG. 7, in the second etching step S12, the second member 62 may be etched to form the buffer space 44, and thus the buffer space 44 is connected to the connecting line 43.

As illustrated in FIG. 8, the method for manufacturing the acoustic control member may further include a fourth etching step S14 and a third bonding step S23.

In the fourth etching step S14, the fourth member 64 is etched to further form the buffer space 44 having the diameter different from the connecting line 43. Here, at least one fourth member 64 may be etched considering a depth of the buffer space 44, and the plurality of fourth members 64 may be sequentially and vertically bonded via the bonding member 66.

In the third bonding step S23, the second member 62 and the fourth member 64 are alternately bonded with each other via the bonding member 66 based on a position of the buffer space 44.

Then, in the first bonding step S21, the first member 61 is vertically bonded via the bonding member 66, on a first surface of the base member after the third bonding step S23, and in the second bonding step S22, the third member 63 is vertically bonded via the bonding member 66, on a second surface of the base member after the third bonding step S23. Thus, the acoustic control member 40 may be completed.

In the matching charging step S31, the impedance matching member 30 is charged to the first signal transmitting groove 41, the second signal transmitting groove 42 and the connecting line 43. The impedance matching member 30 is charged after the bonding of the members are completed, and thus the impedance matching member 30 is prevented from being inserted or flowed into gaps of the members.

Hereinafter, a method for manufacturing an acoustic control member according to still another example embodiment of the present invention, will be explained.

Figure 9:
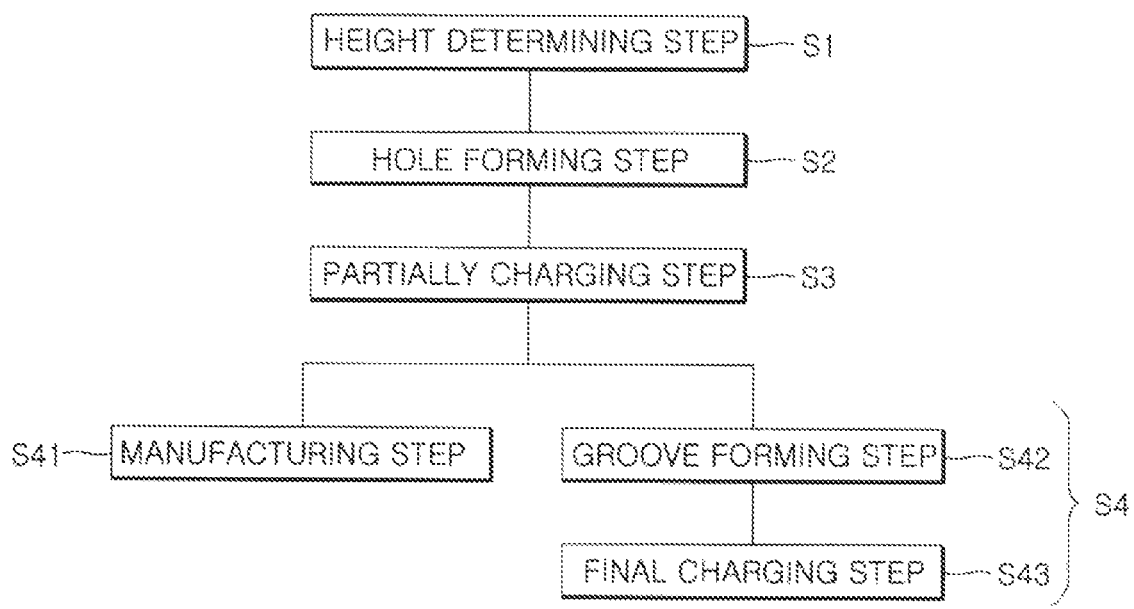
FIG. 9 is a flow chart illustrating a method for manufacturing an acoustic control member according to still another example embodiment of the present invention.
Figure 10:
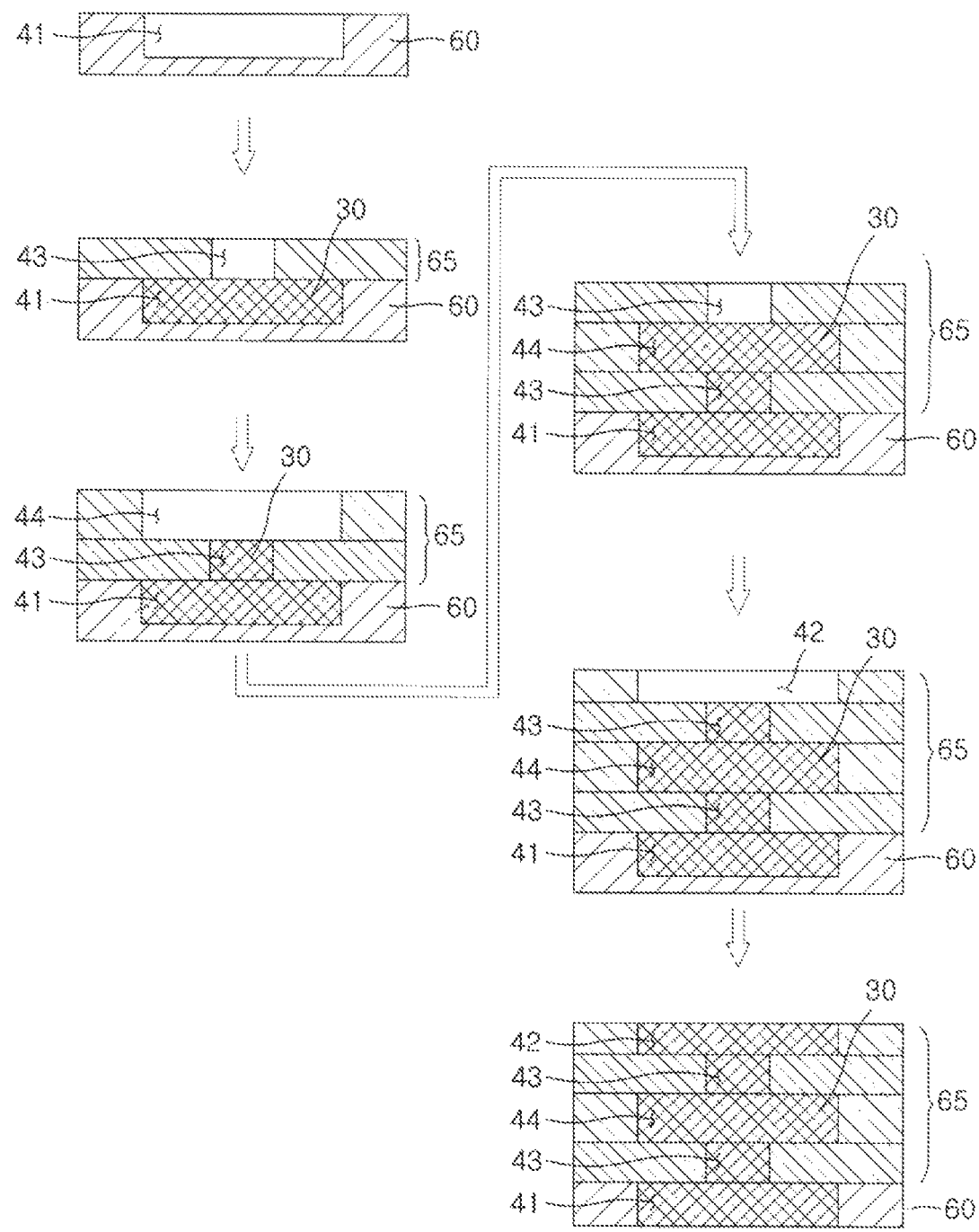
FIG. 10 is a series of cross-sectional views illustrating the method of FIG. 9.
Figure 11:
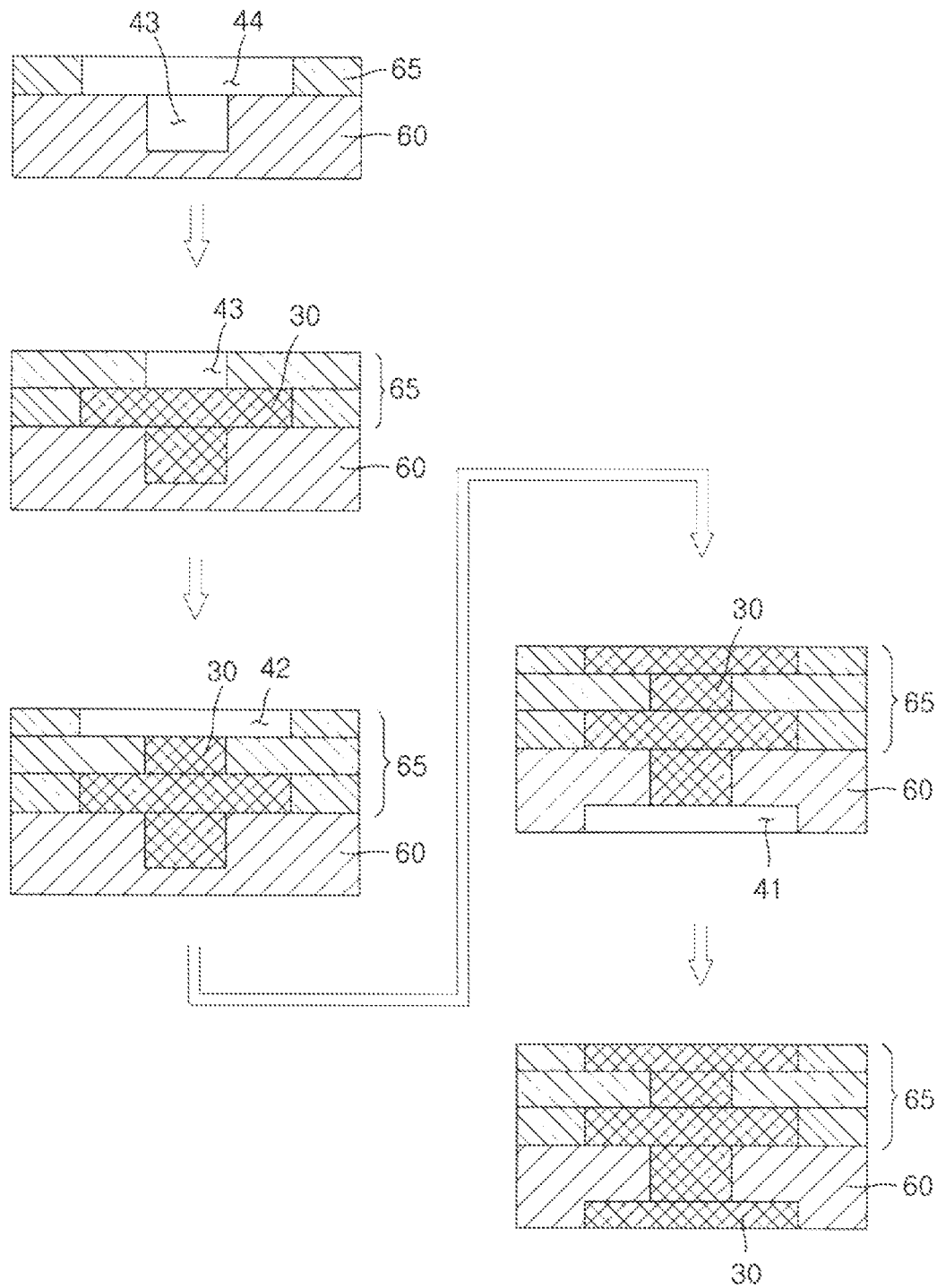
FIG. 11 is another series of cross-sectional views illustrating the method of FIG. 9.

FIG. 9 is a flow chart illustrating a method for manufacturing an acoustic control member according to still another example embodiment of the present invention. FIG. 10 is a series of cross-sectional views illustrating the method of FIG. 9. FIG. 11 is another series of cross-sectional views illustrating the method of FIG. 9.

Referring to FIG. 9, FIG. 10 and FIG. 11, the method for manufacturing the acoustic control member according to the present example embodiment includes, a height determining step S1, a hole forming step S2, a partially charging step S3 and a finishing step S4.

In the height determining step S1, at least two stacked members 65 are sequentially formed on a first surface of the base member 60. Here, the stacked member 65 may include a polymer.

In the hole forming step S2, the base member 60 and the stacked members 65 are respectively etched based on a stacked order of the stacked member 65.

In the partially charging step S3, the impedance matching member 30 is charged to every portion etched in the hole forming step S2.

In the finishing step S4, the base member 60 is manufactured to expose the impedance matching member 30 through a second surface of the base member 60.

Here, the height determining step S1, the hole forming step S2 and the partially charging step S3 are repeated according to a height or a structure of the acoustic control member 40. Here, every stacked member 65 may be etched and the impedance matching member 30 may be charged to every etched portion of the stacked member 65.

For example, the method for manufacturing the acoustic control member according to the present example embodiment, may be performed using the steps illustrated in FIG. 10.

First, in the hole forming step S2, a first surface of the base member 60 is etched to form the first signal transmitting groove 41, and then, in the partially charging step S3, the impedance matching member 30 is charged to the first signal transmitting groove 41 and an upper surface thereof is planarized.

Then, in the height determining step S1, the stacked member 65 is sequentially formed on the base member 60, and the stacked member 65 is etched to form the connecting line 43. In addition, in the partially charging step S3, the impedance matching member 30 is charged to the connecting line 43, and an upper surface thereof is planarized.

Then, in the height determining step S1 additionally, the stacked member 65 is additionally formed, and the additional stacked member 65 is etched to form the buffer space 44. In addition, in the partially charging step S3, the impedance matching member 30 is charged to the buffer space 44, and an upper surface thereof is planarized.

Then, in the height determining step S1 additionally, the stacked member 65 is additionally formed, and the additional stacked member 65 is etched to form the connecting line 43 additionally. In addition, in the partially charging step S3, the impedance matching member 30 is charged to the additional connecting line 43, and an upper surface thereof is planarized.

Then, in the height determining step S1 additionally, the stacked member 65 is additionally formed, and the additional stacked member 65 is etched to form the second signal transmitting groove 43. In addition, in the partially charging step S3, the impedance matching member 30 is charged to the second signal transmitting groove 42, and an upper surface thereof is planarized.

Finally, the finishing step S4 includes a manufacturing step S41 in which the second surface of the base member 60 is entirely etched to expose the impedance matching member 30. Then, the impedance matching member 30 charged to the first signal transmitting groove 41 is exposed, and the acoustic control member 40 is completed.

Alternatively, the method for manufacturing the acoustic control member may be performed as illustrated in FIG. 11.

First, in the height determining step S1, the stacked member 65 is formed on the first surface of the base member 60, and in the hole forming step S2, the stacked member 65 and the base member 60 are sequentially etched to form the buffer space 44 in the stacked member 65, and to form the connecting line 43 in the base member 60. Then, in the partially charging step S3, the impedance matching member 30 is charged to the buffer space 44 and the connecting line 43, and then an upper surface thereof is planarized.

Then, in the height determining step S1 additionally, the stacked member 65 is additionally formed, and the additional stacked member 65 is etched to form the connecting line 43 additionally. In addition, in the partially charging step S3, the impedance matching member 30 is charged to the additional connecting line 43, and then an upper surface thereof is planarized.

Then, in the height determining step S1 additionally, the stacked member 65 is additionally formed, and the additional stacked member 65 is etched to form the second signal transmitting groove 42. In addition, in the partially charging step S3, the impedance matching member 30 is charged to the second signal transmitting groove 42, and then an upper surface thereof is planarized.

Finally, the finishing step S4 includes a groove forming step S42, and a final charging step S43. In the groove forming step S42, a groove is formed on the second surface of the base member 60 to expose the impedance matching member 30. In the final charging step S43, the impedance matching member 30 is charged to the groove formed in the groove forming step 43. Then, in the groove forming step S42, the groove is formed on the second surface of the base member 60 to form the first signal transmitting groove 41, and the impedance matching member 30 charged to the connecting line 43 is exposed in the first signal transmitting groove 41. In addition, the impedance matching member 30 is charged to the first signal transmitting groove 41, and then the acoustic control member 40 is completed. Here, the second surface of the base member 60 may be planarized.

According to the present example embodiments, sensibility of the signal processor 50 is increased to increase a recognition rate of the ultrasonic wave and to increase a reliability for recognizing the fingerprint F.

In addition, transmissivity of the ultrasonic wave, reflectivity of a reverberation wave and transmittance of a destruction wave are increased according to a combination of the contact member 10, the impedance matching member 30 and the acoustic control member 40.

In addition, even though a wavelength and an amplitude of the destruction wave is decreased because of the reflection of the ultrasonic wave due to the fingerprint F, the destruction wave may be stably transmitted to the signal processor 50.

In addition, the ultrasonic wave incident from the acoustic control member 40 is stably transmitted, the ultrasonic wave is induced to be resonated in the acoustic control member 40, and the incident ultrasonic wave is amplified, so that the ultrasonic wave may be stably transmitted between the contact member 10 and the signal processor 50.

In addition, the impedance matching member 30 is charged to the etched portion of the acoustic control member 40, so that the ultrasonic wave may be prevented from being attenuated and may be amplified.

In addition, the security in recognition of the fingerprint F by the electronic device may be increased and the person information stored in the electronic device may be stably protected.

In addition, a micro machining may be performed to control the acoustic in the ultrasonic range, so that the acoustic control member 40 may be easily manufactured.

In addition, each structure having each function in the stacked structure of the acoustic control member may be classified in detail, and the stacking and the bonding between the members of the acoustic control member 40 may be easily performed.

In addition, a centering between the first signal transmitting groove 41, the second signal transmitting groove 42 and the connecting line 43 formed in the acoustic control member 40 may be easily performed, and stacking error may be minimized to increase the reliability of the acoustic control member 40.

In addition, the height of the acoustic control member 40 may be decreased, and thus the module 100 for detecting the fingerprint may be minimized and manufactured with relatively thinner thickness.

In addition, the impedance matching member 30 is charged to the acoustic control member 40, and thus the impedance matching may be more increased in transmitting the ultrasonic wave, the structure of the acoustic control member 40 may be more strengthened, and the structure may be more stably formed.

In addition, sweat pores, and valley V and ridge R of the finger may be correctly detected to simulate a stereoscopic image of the fingerprint F.

In addition, the fingerprint F may be recognized even though contaminants such as a dust, a sweat, a remained cosmetics and so on remain on the fingerprint F. The fingerprint F may be easily recognized regardless of the material of the contact member 10 on which the fingerprint contacts, and thus the module 100 may be manufactured with various kinds of designs.

In addition, the stereoscopic image may be obtained including a dermis layer and an epidermis layer of the fingerprint F of human beings, and the real fingerprint F and the counterfeit fingerprint F' may be easily recognized to increase the security.

In addition, the electronic device may have more increased security via extracting the characteristics of the fingerprint F to be registered and certificated. Thus, high resolution fingerprint technology may be performed based on a low power ultrasonic wave.

In addition, the transducer 20 uses PMUT so that the power of the ultrasonic wave may be more increased and the structure thereof may be more simplified, compared to CMUT.

In addition, the destruction wave disappearing in the reverberation wave in the fingerprint F is amplified and is transmitted to the transducer 20, and the signal processor 50 stably senses the destruction wave to increase the resolution of the image. Thus, the fingerprint F image may be obtained more correctly with the same source as the conventional ultrasonic wave, the signal processor 50 having relatively lower capacity may be used, and power consumption may be decreased.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A module for detecting a fingerprint, the module comprising:
    a contact member with which a fingerprint makes contact;
    a transducer configured to output an ultrasonic signal to the contact member and receive the ultrasonic signal reflected from the contact member;
    an impedance matching member charged between the contact member and the transducer, to transmit the ultrasonic signal between the contact member and the transducer;
    an acoustic control member inserted between the contact member and the transducer, the impedance matching member being charged inside of the acoustic control member;
    a hole penetrating the acoustic control member; and
    a signal processor electrically contacted with the transducer and configured to sense the fingerprint based on the received ultrasonic signal,
    wherein the hole comprises:
        a first signal transmitting groove formed on an upper portion of the acoustic control member, the upper portion facing the contact member;
        a second signal transmitting groove formed on a lower portion of the acoustic control member, the lower portion facing the transducer; and
        a connecting line connecting the first signal transmitting groove with the second signal transmitting groove to penetrate the acoustic control member from the upper portion to the lower portion.

2. The module of claim 1, wherein the impedance matching member comprises:
    a first matching member charged to the acoustic control member; and
    a second matching member charged between the contact member and the acoustic control member, or between the acoustic control member and the transducer.

3. The module of claim 1, wherein the impedance matching member is charged to the first signal transmitting groove, the second signal transmitting groove and the connecting line.

4. An electronic device comprising:
    a detecting module comprising:
        a contact member with which a fingerprint makes contact;
        a transducer configured to output an ultrasonic signal to the contact member and receive the ultrasonic signal reflected from the contact member;
        an impedance matching member charged between the contact member and the transducer, to transmit the ultrasonic signal between the contact member and the transducer;
        an acoustic control member inserted between the contact member and the transducer, the impedance matching member being charged inside of the acoustic control member;
        a hole penetrating the acoustic control member; and a signal processor electrically contacted with the transducer, and configured to control the transducer and detect the fingerprint based on the received ultrasonic signal;

a converting controller connected with the signal processor and configured to convert a signal detected by the signal processor and transmit the converted signal; and a main controller connected with the converting controller and configured to control the detecting module based on the converted signal, wherein the hole comprises:

a first signal transmitting groove formed on an upper portion of the acoustic control member, the upper portion facing the contact member;

a second signal transmitting groove formed on a lower portion of the acoustic control member, the lower portion facing the transducer; and a connecting line connecting the first signal transmitting groove with the second signal transmitting groove to penetrate the acoustic control member from the upper portion to the lower portion.

5. A method for manufacturing an acoustic control member, the method comprising:

a first etching step in which a first member is etched to form a first signal transmitting groove;

a second etching step in which a second member is etched to form a connecting line;

a third etching step in which a third member is etched to form a second signal transmitting groove;

a first bonding step in which the first member is bonded with the second member via a first bonding member;

a second bonding step in which the second member is bonded with the third member via a second bonding member; and a matching charging step in which an impedance matching member is charged to the first signal transmitting groove, the second signal transmitting groove and the connecting line.

6. The method of claim 5, wherein in the first etching step, the first member is etched to further form the connecting line partially.

7. The method of claim 5, wherein in the third etching step, the third member is etched to further form the connecting line partially.

8. The method of claim 5, wherein in the second etching step, the second member is etched to further form a buffer space having a diameter different from the connecting line.

9. The method of claim 5, the method further comprising:

a fourth etching step in which a fourth member is etched to further form a buffer space having a diameter different from the connecting line; and a third bonding step in which the second member and the fourth member are alternately bonded with each other via the bonding member based on a position of the buffer space, wherein in the first bonding step, the first member is bonded on a first surface of a base member after the third bonding step, via the bonding member, wherein in the second bonding step, the third member is bonded on second surface of the base member after the third bonding step, via the bonding member.

10. A method for manufacturing an acoustic control member, the method comprising:

a height determining step in which at least two stacked members are sequentially formed on a first surface of a base member;

a hole forming step in which the base member and the stacked members are respectively etched based on a stacked order of the stacked members;

a partially charging step in which an impedance matching member is charged to every portion etched in the hole forming step; and a finishing step in which the base member is etched to expose the impedance matching member through a second surface of the base member, wherein the height determining step, the hole forming step and the partially charging step are repeated according to a height of the acoustic control member.

11. The method of claim 10, wherein the finishing step comprises:

a manufacturing step in which the second surface of the base member is entirely etched to expose the impedance matching member.

12. The method of claim 10, wherein the finishing step further comprises:

a groove forming step in which a groove is formed on the second surface of the base member to expose the impedance matching member; and a final charging step in which the impedance matching member is charged to the groove formed in the groove forming step.

* * * * *